(12) United States Patent
Dlamini et al.

(10) Patent No.: US 11,147,256 B2
(45) Date of Patent: Oct. 19, 2021

(54) MONITORING DISEASE VECTORS (71) Applicant: International Business Machines Corporation, Armonk, NY (US)

(72) Inventors: Gciniwe Simphiwe Dlamini, Johannesburg (ZA); Darlington Shingirirai Mapiye, Randburg (ZA); James Mashiyane, Selcourt (ZA)

(73) Assignee: International Business Machines Corporation, Armonk, NY (US)

( * ) Notice: Subject to any disclaimer, the term of this patent is extended or adjusted under 35 U.S.C. 154(b) by 410 days.

(21) Appl. No.: 16/207,223

(22) Filed: Dec. 3, 2018

(65) Prior Publication Data
US 2020/0170234 A1 Jun. 4, 2020

(51) Int. Cl.
*G16H 50/80* (2018.01)
*A01M 1/02* (2006.01)
*A01M 1/22* (2006.01)
*G06K 9/62* (2006.01)

(52) U.S. Cl.
CPC .............. *A01M 1/026* (2013.01); *A01M 1/22* (2013.01); *G06K 9/6289* (2013.01); *G16H 50/80* (2018.01); *A01M 2200/01* (2013.01)

(58) Field of Classification Search
CPC .... A01M 1/026; A01M 1/22; A01M 2200/01; G06K 9/6289; G16H 50/80
USPC ........................................................ 43/132.1
See application file for complete search history.

(56) References Cited

U.S. PATENT DOCUMENTS

| 5,005,416 A | 4/1991 | Vick et al. |
| 5,241,778 A | 9/1993 | Price |
| 5,473,942 A | 12/1995 | Vick et al. |

(Continued)

FOREIGN PATENT DOCUMENTS

| WO | 2016168347 | 10/2016 |
| WO | 2017120189 | 7/2017 |

OTHER PUBLICATIONS

John Garth, "Acoustic mosquito detector to aid campaign against tropical diseases", Oct. 6, 2017, Medium (retrieved Dec. 3, 2018). Available at: https://medium.com/oxford-university/acoustic-mosquito-detector-to-aid-campaign-against-tropical-diseases-616630a1ab3.

*Primary Examiner* — Claude J Brown
(74) *Attorney, Agent, or Firm* — Shimon Benjamin; Otterstedt, Wallace & Kammer, LLP (57) ABSTRACT

A computer-implemented method for monitoring disease vectors is disclosed. A vector sensor obtains vector data relating to disease vectors in a monitored area. An environmental data obtaining component obtains environmental data relating to the monitored area. Based on at least one of the vector data and the environmental data, a population characteristic component may estimate or determine a vector population characteristic associated with the monitored area. A structural data obtaining component may obtain structural data relating to the monitored area. A vector travel estimation component may estimate or determine a vector travel characteristic. The vector characteristic may be indicative of predicted disease vector movement from outdoors to indoors in the monitored area and may allow for or facilitate a vector control action based at least partially on the vector travel characteristic. A device and a system for monitoring disease vectors are also disclosed.

20 Claims, 4 Drawing Sheets

(56) References Cited

U.S. PATENT DOCUMENTS

| | | | |
|---|---|---|---|
| 6,766,251 B2* | 7/2004 | Mafra-Neto | A01B 79/005 |
| | | | 702/5 |
| 7,057,516 B2 | 6/2006 | Donskoy et al. | |
| 7,656,300 B2* | 2/2010 | Ronnau | A01M 1/026 |
| | | | 340/573.2 |
| 9,585,376 B2 | 3/2017 | Park et al. | |
| 10,524,461 B1* | 1/2020 | Files | G06F 9/542 |
| 2010/0134301 A1* | 6/2010 | Borth | G08C 17/02 |
| | | | 340/573.2 |
| 2010/0186284 A1 | 7/2010 | Hyde et al. | |
| 2012/0306683 A1 | 12/2012 | Viikari | |
| 2013/0167429 A1 | 7/2013 | Tseng | |
| 2013/0259846 A1 | 10/2013 | Dobson | |
| 2016/0245916 A1* | 8/2016 | Weber-Grabau | G01B 11/08 |
| 2017/0049092 A1 | 2/2017 | Osseiran | |
| 2017/0223943 A1 | 8/2017 | Park et al. | |
| 2017/0281822 A1* | 10/2017 | Becker | A61L 9/12 |
| 2018/0293869 A1* | 10/2018 | Padhye | G08B 21/10 |
| 2018/0299842 A1* | 10/2018 | Reid | A01M 31/002 |
| 2019/0246623 A1* | 8/2019 | Tews | A01M 29/00 |

\* cited by examiner

MONITORING DISEASE VECTORS

BACKGROUND

The present invention relates to the monitoring of disease vectors and it relates specifically to a method and device for monitoring disease vectors which facilitates vector control interventions.

The term "disease vector" refers to an agent that carries and may transmit an infectious pathogen to another living organism. Certain insects may be disease vectors. Insect-borne diseases may place serious health and economic burdens on individuals, families, communities, corporate entities and/or countries, especially in low- and middle-income regions.

In the context of this specification, the term "disease vector" or "disease vectors" should be broadly interpreted and may refer to an agent or agents of a single type of vector (e.g., mosquitos) or to an agent or agents of multiple types of vectors.

SUMMARY

According to an example embodiment of the present invention, there is provided a computer-implemented method comprising obtaining, by at least one vector sensor, vector data relating to disease vectors in a monitored area and obtaining, by at least one environmental data obtaining component, environmental data relating to the monitored area. Based on at least one of the vector data and the environmental data, a population characteristic component may estimate or determine a vector population characteristic associated with the monitored area. The method may comprise obtaining, by a structural data obtaining component, structural data relating to the monitored area. The structural data may include data relating to at least one building in or near the monitored area. The method may further comprise estimating or determining, by a vector travel estimation component, a vector travel characteristic. The vector travel characteristic may be based on the structural data and at least one of the vector data, the environmental data and the vector population characteristic. The vector travel characteristic may be indicative of predicted vector movement from outdoors to indoors in the monitored area. This may allow for or facilitate a vector control action based at least partially on the vector travel characteristic.

Example embodiments of the present invention extend to a corresponding device and to a corresponding a system.

DETAILED DESCRIPTION

Figure 1:
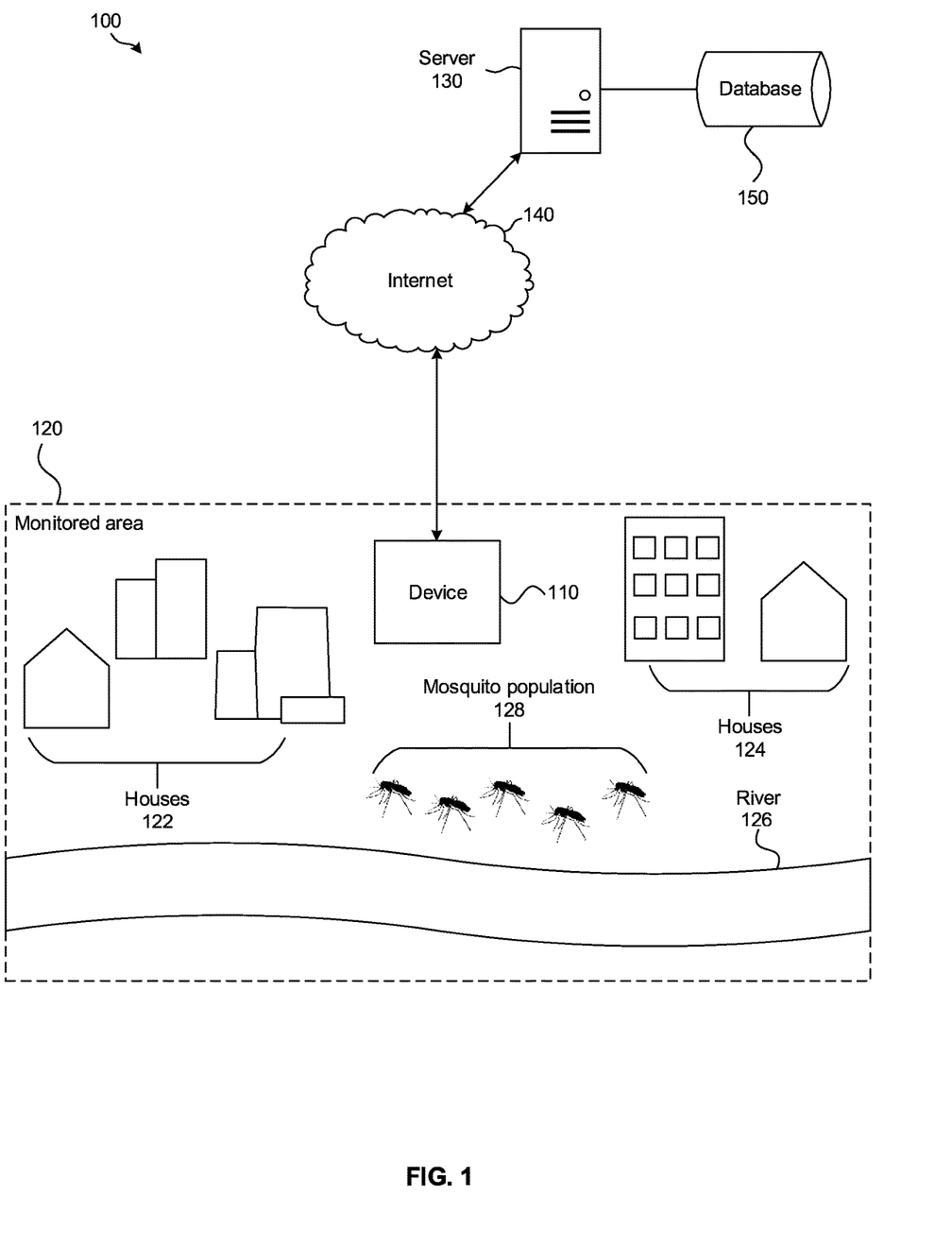
FIG. 1 schematically illustrates a network topology which includes a device for monitoring disease vectors in accordance with an embodiment of the invention, wherein the device is installed in a monitored area.

The topology 100 of FIG. 1 includes an example embodiment of a device for monitoring disease vectors (hereinafter referred to as "the device 110"). In this example, the device 110 is a so-called IoT (Internet of Things) enabled device which is communicatively coupled to a remotely accessible server 130 via the Internet 140. The server 130 is in turn communicatively coupled to a database 150 which stores data that may be used by the device 110 in the monitoring of disease vectors.

The device 110 may be installed in a monitored area 120 (hereinafter referred to as "the area 120") to monitor disease vectors in the area 120. In this example, the area 120 includes houses 122, 124 that are located in close proximity to a body of water in the form of a river 126. The houses 122, 124 may have different structures and structural features, e.g. different sizes and layouts, as shown in FIG. 1, different levels of insulation, etc.

In some embodiments, the device 110 may be used to monitor other types of buildings, e.g. hospitals and/or schools, alternatively or in addition to houses, and embodiments of the invention are therefore not restricted to the monitoring of houses.

The device 110, or a plurality of these devices, may be positioned according to monitoring needs. One device may be positioned specifically to monitor a set or cluster of houses (e.g. the houses 122). For instance, one device may be used to monitor the houses 122 while another device is dedicated to monitoring the houses 124. In some cases, a dedicated device may be used for each building or structure. Alternatively, and as will be described with reference to FIG. 1, the device 110 may monitor a "monitored area" such as the monitored area 120. In the context of this specification, the term "monitored area" or "area" should thus be interpreted broadly and may refer to any suitable monitoring arrangement, including any of the monitoring arrangements referred to above.

Turning again to FIG. 1, the area 120 may include disease vectors in the form of a mosquito population 128. Throughout this description, reference will be made to mosquitos for illustrative purposes, but it will be understood that embodiments of the invention may be applied to the monitoring of other types of disease vectors, e.g., other insects such as tsetse flies, fleas or ticks, or other animals such as mammals. One type of disease vector is monitored by this example device 110, but in other embodiments the device may be configured to monitor multiple types of vectors (e.g. multiple different species).

The device 110 may include various structural and functional components. Examples of these components are illustrated by the block diagram 200 of FIG. 2.

Figure 2:
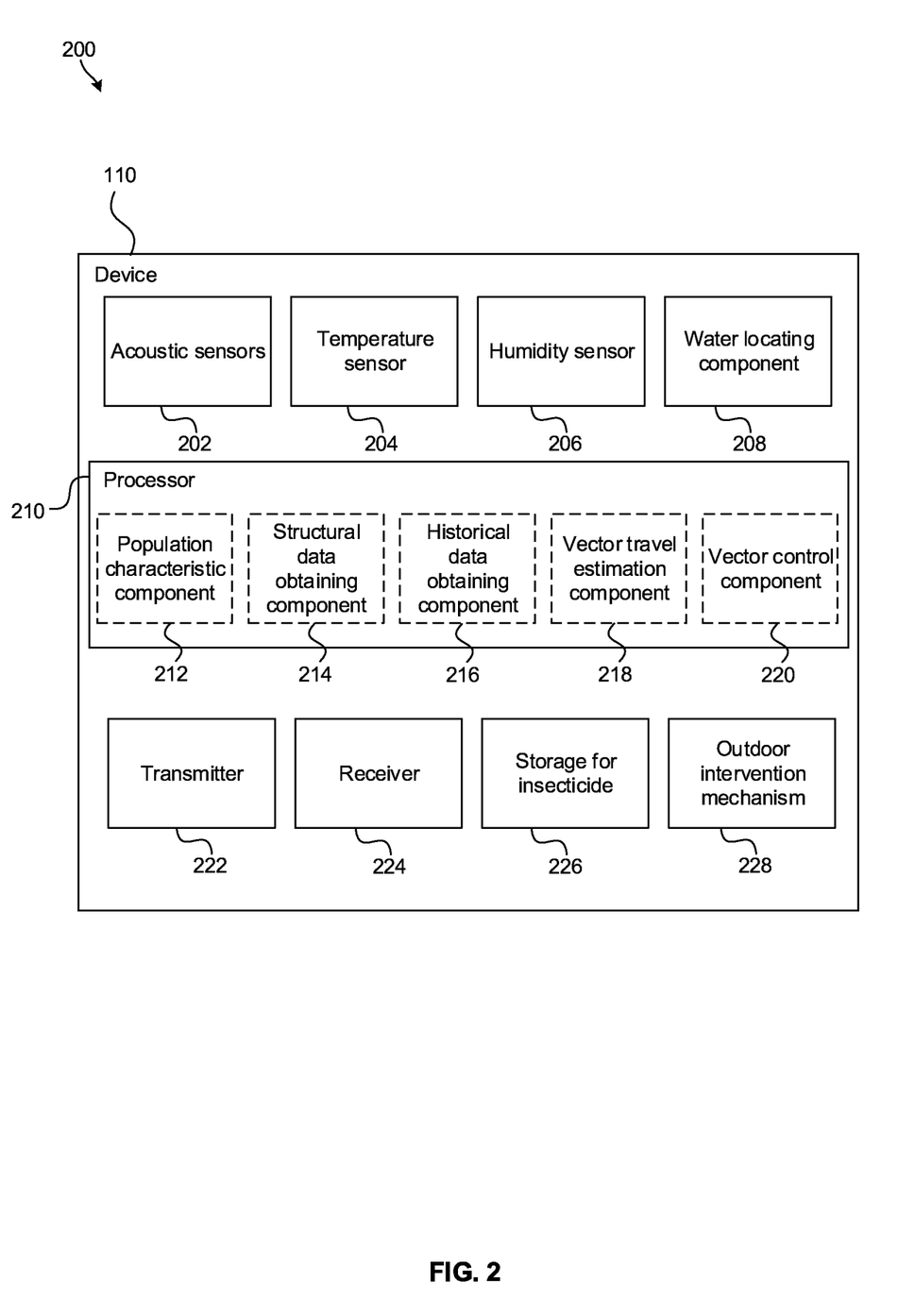
FIG. 2 illustrates a block diagram of example components of the device of FIG. 1.

The device 110 may include at least one vector sensor. In this example, acoustic sensors 202 are used as vector sensors. The acoustic sensors 202 may be configured to obtain vector data relating to the mosquito population 128. For instance, the sensors 202 may include a microphone array which carries out digital signal processing (DSP) (e.g., filtering, separation and discrimination) so as to localize mosquitos and/or determine the number of mosquitos in a specific zone, e.g. localize and quantify the mosquito population 128.

The device 110 may also include environmental data obtaining components. The environmental data obtaining components shown in the example of FIG. 2 are a temperature sensor 204, a humidity sensor 206 and a water locating component 208. The temperature sensor 204 and humidity sensor 206 may monitor temperature and humidity, respectively, in the area 120 (e.g. in proximity to the device 110).

The water locating component 208 may include a Global Positioning System (GPS) based system capable of localizing bodies of water and/or determining the distance from the device 110 to a body of water.

In some embodiments, instead of actively monitoring the environmental factors or conditions referred to above, some or all of the necessary data may be pulled or otherwise obtained from a remote source, e.g., from the sever 130 or database 150 via the Internet.

The device 110 may further include a computer processor 210 which may be communicatively coupled to the other components of the device 110, e.g. the acoustic sensors 202, temperature sensor 204, humidity sensor 206 and water locating component 208. The device 110 may include a storage medium which stores a set of instructions to direct operation of the processor 210. When executing the instructions, the processor 210 may comprise a number of functional/logical components or modules. In the example of FIG. 2, the processor 210 may comprise a population characteristic component 212, a structural data obtaining component 214, a historical data obtaining component 216, a vector travel estimation component 218 and a vector control component 220.

The population characteristic component 212 may be configured to estimate or determine a vector population characteristic associated with the area 120 or with the mosquito population 128. In this example, the population characteristic component 212 may be configured to analyse the vector data obtained by the acoustic sensors 202, the environmental data obtained by the water locating component 208 and/or data obtained by the sensors 204, 206 to estimate a vector population characteristic in the form of a population density of the mosquito population 128. The population density may, in some embodiments, specifically refer to outdoor population density. The vector population characteristic may be or include other characteristics, e.g., total population, population growth rate, or the like.

The structural data obtaining component 214 may be configured to obtain structural data relating to the area 120. This may include data relating to buildings, e.g. the houses 122, 124, in the area 120. In this example, the database 150 stores the necessary information on the houses 122, 124, including their locations, their distribution, their structural features (e.g., brick or mud, a measure of insulation, or the like). The device 110 may obtain the structural data from the database 150 via the Internet 140 and a receiver 224 of the device 110.

The database 150 may be prepopulated with the structural data. This may be achieved by way of techniques such as image processing and natural language processing.

The historical data obtaining component 216 may be configured to obtain historical disease vector data and/or historical disease data for the area 120 or an associated area. For instance, information on previously measured rates of travel of vectors (e.g. rate of travel of mosquitos in still air), rates of infection (e.g., malaria infection), seasonal trends, historic disease trends, data on insect numbers and historical population densities, or the like, may be obtained. In this example, the database 150 stores the necessary historical data which may be obtained by the device 110 via the Internet and the receiver 224.

In other embodiments, the database 150 may form part of the device 110 and the necessary structural and/or historical data (or other data) may thus be obtained locally.

The vector travel estimation component 218 may be configured to estimate or determine a vector travel characteristic. This estimation or determination may be made based on the abovementioned structural data and at least one of the vector data, the environmental data and the vector population characteristic. The historical disease vector data and/or the historical disease data referred to above may also be employed to arrive at the vector travel characteristic.

The vector travel characteristic may be indicative of predicted disease vector movement from outdoors to indoors in the monitored area, e.g., from outside of the houses 122, 124 to inside the houses 122, 124. In this example, the vector travel characteristic is an estimated rate at which disease vectors may travel from outdoors to indoors in the monitored area. In other embodiments, a different vector travel characteristic may be used, e.g., an estimated vector population level, a risk level associated with possible movement from outdoors to indoors, or the like. Combinations of characteristics or values may also be employed.

The vector control component 220 may be configured to initiate a vector control action, which may be an indoor action and/or an outdoor action. The vector control action which is initiated, or implemented, may be based at least partially on the vector travel characteristic referred to above. In other words, based on the estimated severity of the threat posed by the disease vector, commensurate action may be taken/initiated.

The vector control component 220 may cause a transmitting component in the form of a transmitter 222 of the device 110 to transmit an electronic indoor action request to a predefined entity, which may include instructions for controlling, repelling or eliminating disease vectors indoors in the area 120. For instance, a text message or email may be transmitted with instructions on how to deal with the vector threat inside of the houses 122, 124. The vector control component may be configured to carry out or initiate an outdoor intervention intended to control, repel or eliminate disease vectors in the area 120. These aspects will be described in greater detail below, with reference to FIG. 3.

The device 110 may further include storage space for insecticide 226 and one or more outdoor intervention mechanism 228 for repelling the mosquitos 128.

The transmitter 222, the receiver 224 and the mechanism 228 may also be communicatively coupled to the processor.

The device 110 may be powered by any suitable energy source, e.g. batteries or mains/public electricity supply.

Figure 3:
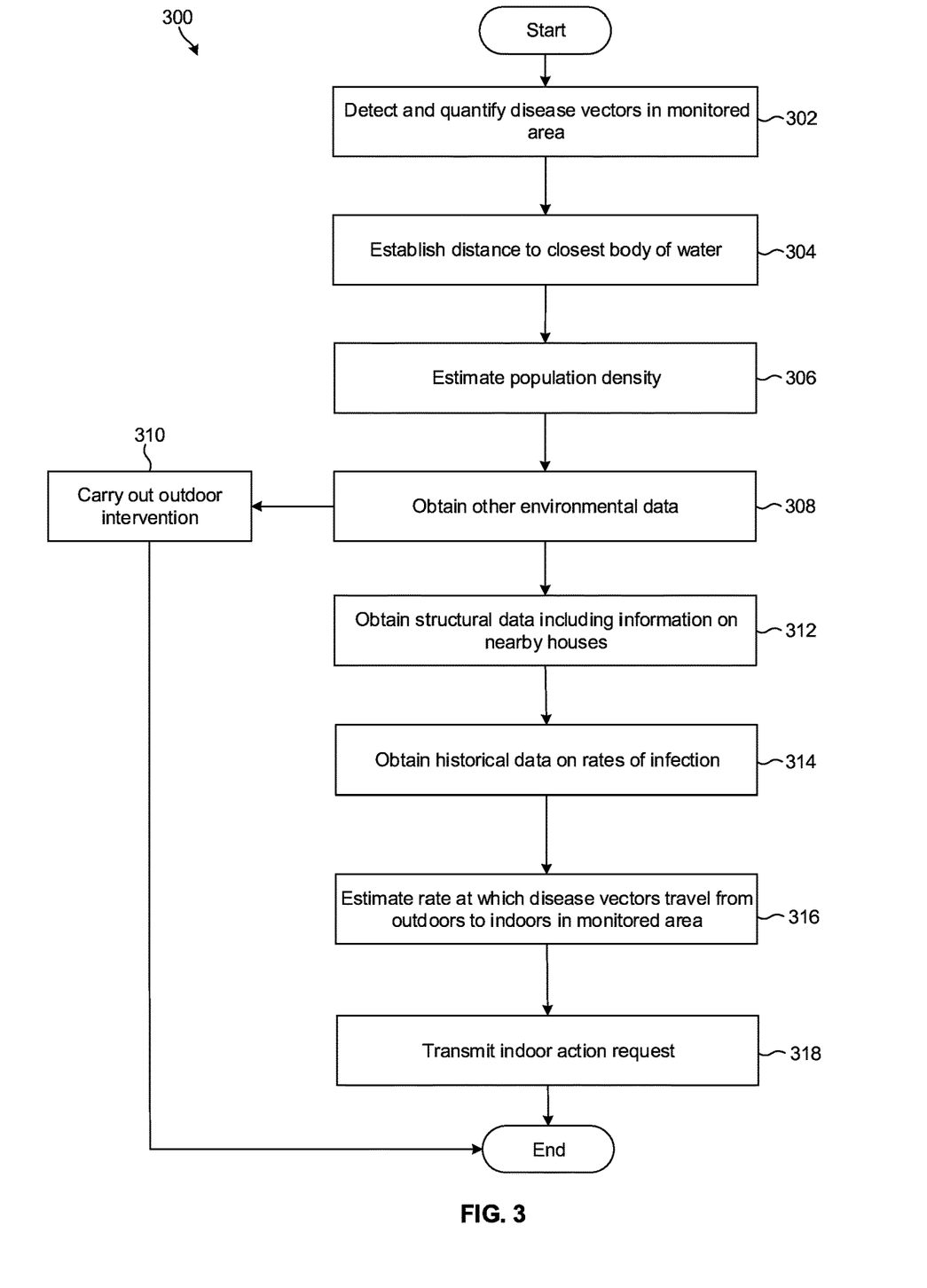
FIG. 3 illustrates a flow diagram of an example of a method of monitoring disease vectors using the example device of FIG. 1, in accordance with an embodiment of the invention.

The flow diagram 300 of FIG. 3 shows an example of a method of monitoring disease vectors using the example device 110 described with reference to FIGS. 1 and 2. The device 110 may be positioned in an area (e.g. the area 120) which is believed to be a problem area in terms of infections via disease-carrying vectors, e.g., a rural village or low-income region with high rates of infections. A plurality of devices 110 may be positioned in a single area.

At stage 302, the acoustic sensors 202 may be used to detect and quantify (e.g. estimate a size of) the mosquito population 128. The sensors 202 may be configured to differentiate mosquito signals from other sounds/signals (refer to the example described with reference to FIG. 4 below).

The water locating component 208 may be used to detect the location of and/or determine the distance to the river 126 (stage 304). The water locating component 208 may be configured to detect, determine distance to and/or map various bodies of the water in an area.

At stage 306, the population characteristic component 212 may estimate the population density of the mosquito population 128 based on the data obtained in previous stage 302 and/or stage 304. In other embodiments, more and/or different inputs may be used, e.g. historical data, other environmental data such as humidity, temperature, or the like. An example of a manner in which population density may be estimated will be described in greater detail with reference to FIG. 4.

In addition to environmental data relating to water, the sensors 202, 204 may be used to measure temperature and humidity in the area 120 (stage 308). Further environmental data may also be obtained, e.g., weather data like wind speed and/or wind direction. At stage 310, based on the estimated population density and the environmental data obtained in stage 308, it may be determined that outdoor intervention is required. In some embodiments, an outdoor risk factor may be determined by the processor 120.

A threshold may be set and, if the risk factor or level exceeds the threshold, outdoor intervention may be required. In some cases, it may be determined that outdoor intervention is not required, e.g. if the outdoor risk factor is sufficiently low in light of a small vector population and/or favourable weather conditions.

The vector control component 220 may initiate outdoor control action (stage 310). For instance, the mechanism 228 may be actuated to spray insecticide from the storage 226. In cases where vectors may be repelled by way of sound, the device 110 may include a speaker which may emit signals known to repel such vectors. The abundance of the vector, as determined by the processor 210, may determine the extent of outdoor control action required.

The structural data obtaining component 214 may obtain details of the houses 122, 124 (stage 312) and the historical data obtaining component 216 may obtain historical data, e.g. measures travelling speeds of vectors and/or recent rates of malaria infection in the region (stage 314).

Based on one more of the estimated population density, environmental and/or weather conditions, the structural data and the historical data obtained, the rate at which mosquitos travel from outdoors to indoors may be estimated by the vector travel estimation component 218 of the processor 210 (stage 316).

Based on this rate, the processor 210 may cause an appropriate indoor action request to be transmitted to a predefined entity (stage 318). The indoor action request may be a request to sent to local health facilities for additional indoor intervention in the houses 122, 124 and/or in other structures. The request may provide information on, for instance, how much residual indoor spraying to do in affected areas, how many nets (e.g., insecticide coated nets) to distribute, or the like. This may enable effective resource allocation, especially in resource-constrained settings.

The abundance of the vector, rate at which it is predicted to travel into buildings and/or the risk posed to humans, as determined by the processor 210, may determine the extent of indoor action required. A threshold may be applied to the rate as described above. In other words, the indoor action request may be transmitted only if it is determined that the vector travel characteristic is unacceptably high or equites to an unacceptably high risk.

In this example, the device 110 may thus provide an analytics engine estimating the population density of the mosquito population 128 and the rate at which vectors travel from outdoors to indoors in the area 120.

Figure 4:
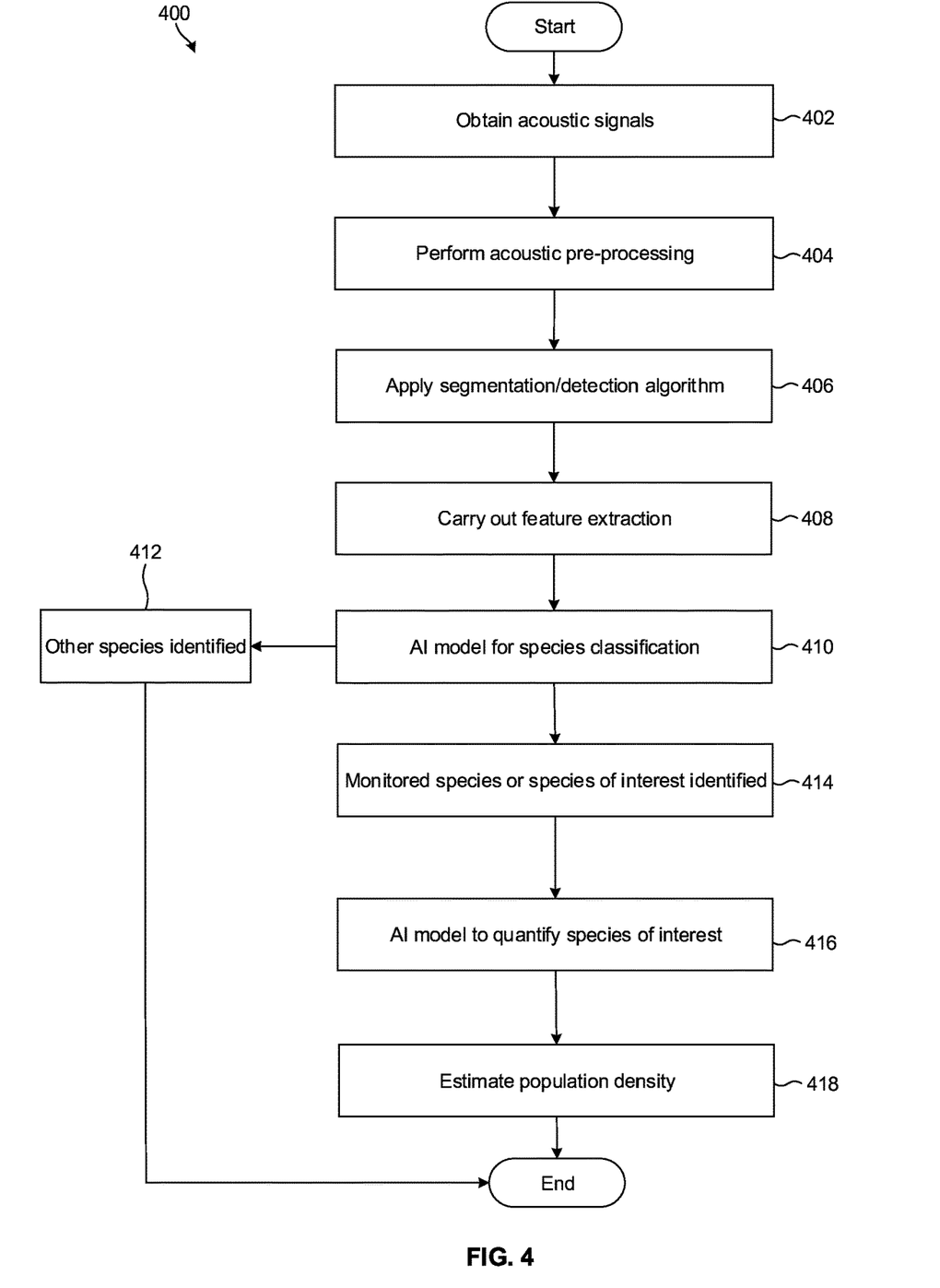
FIG. 4 illustrates a flow diagram of an example of a manner in which population density may be estimated, in accordance with an embodiment of the invention.

The flow diagram 400 of FIG. 4 shows an example of a method of estimating disease vector population, again using the example device 110 described with reference to FIGS. 1 and 2.

At stage 402, acoustic signals are obtained by the acoustic sensors 202. Acoustic pre-processing may then be carried out (stage 404). This may entail using a digital filter to remove background noise. For instance, the device 110 may be configured to remove environmental noise that is not attributable to vector movements. Depending on audio quality, pre-processing may also include one or more of amplification, decimation or up-sampling to change the sampling rate of a signal or signals.

A segmentation/detection algorithm may then be applied (stage 406). This may include isolating parts of the filtered signal into short clips that actually contain some signal. Pauses may be removed as they do not contain information that will aid in downstream classification tasks. The detection algorithm may entail finding starting and end points of vector sound activity. These segmented clips may then be used as units of audio classification. During segmentation, the audio clip may be analysed in short windows of a few milliseconds each. If the energy in that short window is above a certain threshold, then that clip may be retained. If not, then the clip may be discarded. The next frame may start immediately where the previous window ends. This process may be continued until an entire audio clip has been analysed. The starting time and end time of all segmented clips may be recorded.

At stage 408, acoustic features may be extracted from each segmented clip. A discrete Fourier transform (DFT) may be computed and used to convert signals from the time domain to the frequency domain. This may be done due to many of the features of interest in acoustic data being found in the frequency domain. The DFT of the signal may then provide a signature for that clip. The DFT may be used directly, or other features may be extracted from it e.g. mean frequency, dominant frequency and/or spectral flatness measure.

At stage 410, an Artificial Intelligence (AI) model for species classification may be employed. The AI model may be configured to employ neural networks and/or Bayesian classifiers to determine whether sounds are emanating from a species of interest, e.g. mosquito. If the AI model determines that a sound is emanating from a species that is not of interest, the data associated with that sound is discarded (stage 412).

On the other hand, if the sound emanates from a species of interest (stage 414), a further AI model may be employed for quantifying this species of interest (stage 416). For instance, the AI model may count unique individuals associated with the mosquito population 128. Additionally, more discriminative features may be computed on clips belonging to the same species. This may entail computing mel-frequency cepstral coefficients (MFCCs).

To compute the MFCCs of an acoustic signal, the discrete Fourier transform of a windowed excerpt of a signal may be taken. Then, mel-frequency warping may be carried out by mapping the powers of the spectrum obtained onto the mel scale, using triangular overlapping windows. Then, log magnitude warping may be carried out by taking the logs of the powers at each of the mel frequencies. Once log magnitude warping has been done, the discrete cosine transform of the list of mel log powers may be taked as if it were a signal. The MFCC vectors are the amplitudes of the resulting spectrum.

After the population has been estimated (e.g. in the manner described above), the density may be estimate (stage 418). For instance, if s is the population size that was estimated, and α is the survey area for the device 110, then the density D of vectors in the area 120 may be calculated using the following formula:

$$D = \frac{s}{a} * \lambda$$

For example, λ (alpha) may refer to a set of multipliers that may be used to account for inaccuracies, e.g. false negative detections. These multipliers may be estimated during experimentation or during device setup. Other density estimation methods may be employed, e.g. assuming a specific probabilistic distribution of certain vector characteristics.

In the example described with reference to FIG. 4, the quantified population density is an outdoor population density. The outdoor population density estimated by the device 110 may be used to estimate vector travel rate. For example, the following variables may be used:

N—estimated outdoor population size of the species of interest;
H—housing structure insulation score (e.g., 1 to 5, where 1 is the lowest level of insulation and 5 is the highest level of insulation);
C—climate condition variable or variables, e.g. wind speed;
d—average distance from the device 110 to the houses in question; and
k—initial rate of travel, to be measured experimentally.

A function $f$ may be employed. This function may take the abovementioned variables and/or other variables into account to provide the estimated rate of travel of the vectors of interest from outdoors to indoors in the area 120. For example, $$f(N, H, C, d, k) = k(t) + \mu\left(\frac{C}{H*d}N\right)$$

where t represents time and μ is a parameter to be determined. It will be appreciated that the function $f$ may take various functional forms and may be adapted according to the monitoring and intervention requirements of a particular implementation.

The Applicant has found that embodiments of the invention may provide numerous advantages.

Embodiments of the invention may permit automatic monitoring of disease vectors and substantially automatic intervention. Embodiments of the invention not only provide monitoring and quantification features but may enable users to achieve effective and targeted interventions. In some embodiments, both indoor and outdoor intervention is carried out, permitted or facilitated.

Embodiments of the invention may utilise data such as outdoor population density of a disease vector and structural data (e.g. housing structure data) in an area to estimate a rate at which disease vectors are likely to travel indoors and to allow for relatively precise vector elimination. This may ensure that suitable recommendations are made in respect of precautions and/or action to prevent or reduce infections. For instance, mosquito-borne illnesses such as malaria, yellow fever, Zika fever, dengue and/or West Nile virus, or sleeping sickness (African trypanosomiasis) which may be carried by tsetse flies, may be prevented or infections may be reduced.

Embodiments of the invention may allow for reaction to threats posed by disease vectors, swiftly or substantially in real-time, and both outdoors and indoors, at least in some implementations. Different intervention modalities may be utilised, e.g. stationary components, non-stationary components and/or human intervention. Environmental factors may be considered to determine the optimal intervention strategy.

Embodiments of the invention may reduce disease vector populations and/or reduce transmission of insect-borne diseases. As a result, health, productivity and socio-economic conditions may be improved. Furthermore, embodiments of the invention may be implemented to reduce the risk of product contamination by insects, e.g. food and pharmaceutical contamination.

Embodiments of the invention may provide an IoT device or system which is capable of drawing data, e.g. historic disease data or data on houses in an area, from a source via the Internet in order to estimate population and/or disease travel characteristics.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. The term "component" as used herein may refer to a module.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
   obtaining, by at least one vector sensor, vector data relating to disease vectors in a monitored area;
   obtaining, by at least one environmental data obtaining component, environmental data relating to the monitored area;
   estimating or determining, by a population characteristic component, based on at least one of the vector data and the environmental data, a vector population characteristic associated with the monitored area;
   obtaining, by a structural data obtaining component, structural data relating to the monitored area, wherein the structural data includes an insulation score relating to at least one building in or near the monitored area; and
   estimating or determining, by a vector travel estimation component, a vector travel characteristic, wherein the vector travel characteristic is based on the structural data and at least one of the vector data, the environmental data and the vector population characteristic, and wherein the vector travel characteristic is indicative of predicted vector movement from outdoors to indoors relative to the at least one building in or near the monitored area, thereby allowing for or facilitating a vector control action based at least partially on the vector travel characteristic.

2. The method according to claim 1, which further includes obtaining, by a historical data obtaining component, historical disease vector data and/or historical disease data for the monitored area or an area associated with the monitored area, wherein the vector travel characteristic is estimated or determined based at least partially on the historical disease vector data and/or the historical disease data.

3. The method according to claim 1, wherein obtaining the vector data further comprises obtaining an acoustic signal using at least one acoustic sensor of the at least one vector sensor.

4. The method according to claim 1, wherein the estimation and determination of the vector population characteristic and the estimation and determination of the vector travel characteristic are based on the environmental data, and wherein obtaining the environmental data further comprises at least one of:
- measuring temperature in the monitored area using a temperature sensor of the environmental data obtaining component;
- measuring humidity in the monitored area using a humidity sensor of the environmental data obtaining component and
- locating or estimating a distance to a body of water using a water locating component of the environmental data obtaining component.

5. The method according to claim 1, wherein the structural data includes at least one of data relating to locations of buildings in or near the monitored area, and data relating to structural features of buildings in or near the monitored area.

6. The method according to claim 1, which further includes initiating, by a vector control component, the vector control action.

7. The method according to claim 6, wherein initiating the vector control action includes electronically transmitting, by a transmitting component, an indoor action request to a predefined entity, wherein the indoor action request includes instructions for controlling, repelling or eliminating the disease vectors indoors in the monitored area.

8. The method according to claim 6, wherein the vector control action includes carrying out an outdoor intervention intended to control, repel or eliminate the disease vectors in the monitored area.

9. The method according to claim 1, wherein the vector travel characteristic is an estimated rate at which the disease vectors travel from the outdoors to the indoors in the monitored area.

10. The method according to claim 1, wherein the disease vectors are insects.

11. A device comprising:
- at least one vector sensor which is configured to obtain vector data relating to disease vectors in a monitored area;
- at least one environmental data obtaining component which is configured to obtain environmental data relating to the monitored area; a population characteristic component which is configured to estimate or determine, based on at least one of the vector data and the environmental data, a vector population characteristic associated with the monitored area;
- a structural data obtaining component which is configured to obtain structural data relating to the monitored area, wherein the structural data includes an insulation score relating to at least one building in or near the monitored area; and
- a vector travel estimation component which is configured to estimate or determine a vector travel characteristic, wherein the vector travel characteristic is based on the structural data and at least one of the vector data, the environmental data and the vector population characteristic, and wherein the vector travel characteristic is indicative of predicted vector movement from outdoors to indoors relative to the at least one building in or near the monitored area, thereby allowing for or facilitating a vector control action based at least partially on the vector travel characteristic.

12. The device according to claim 11, which further includes a historical data obtaining component which is configured to obtain historical disease vector data and/or historical disease data for the monitored area or an area associated with the monitored area, wherein the vector travel estimation component estimates the vector travel characteristic based at least partially on the historical disease vector data and/or the historical disease data.

13. The device according to claim 11, wherein obtaining the vector data further comprises obtaining an acoustic signal using at least one acoustic sensor of the at least one vector sensor.

14. The device according to claim 11, wherein the estimation and determination of the vector population characteristic and the estimation and determination of the vector travel characteristic are based on the environmental data, and wherein obtaining the environmental data further comprises at least one of:
- a temperature sensor for measuring temperature in the monitored area;
- a humidity sensor for measuring humidity in the monitored area; and
- a water locating component for locating or estimating a distance to a body of water.

15. The device according to claim 11, wherein the structural data obtaining component is configured to obtain at least one of data relating to locations of buildings in or near the monitored area, and structural features of buildings in or near the monitored area.

16. The device according to claim 11, which further includes a vector control component which is configured to initiate the vector control action.

17. The device according to claim 16, which further includes a transmitting component, wherein initiating the vector control action includes electronically transmitting, by the transmitting component, an indoor action request to a predefined entity, and wherein the indoor action request includes instructions for controlling, repelling or eliminating the disease vectors indoors in the monitored area.

18. The device according to claim 16, wherein the vector control component is configured to carry out an outdoor intervention intended to control, repel or eliminate the disease vectors in the monitored area.

19. The device according to claim 11, wherein the vector travel characteristic is an estimated rate at which the disease vectors travel from the outdoors to the indoors in the monitored area.

20. A system comprising:
- at least one vector sensor which is configured to obtain vector data relating to disease vectors in a monitored area;
- at least one environmental data obtaining component which is configured to obtain environmental data relating to the monitored area;
- at least one computer processor which is communicatively coupled to the at least one vector sensor and to the at least one environmental data obtaining component; and
- at least one computer readable storage medium having stored thereon program instructions executable by the at least one computer processor to direct operation of the at least one computer processor, wherein the at least one computer processor, when executing the program instructions, comprises:
  - a population characteristic component which is configured to estimate or determine, based on at least one of the vector data and the environmental data, a vector population characteristic associated with the monitored area;
  - a structural data obtaining component which is configured to obtain structural data relating to the monitored area, wherein the structural data includes an insulation score relating to at least one building in or near the monitored area; and a vector travel estimation component which is configured to estimate or determine a vector travel characteristic, wherein the vector travel characteristic is based on the structural data and at least one of the vector data, the environmental data and the vector population characteristic, and wherein the vector travel characteristic is indicative of predicted disease vector movement from outdoors to indoors relative to the at least one building in or near the monitored area, thereby allowing for or facilitating a vector control action based at least partially on the vector travel characteristic.

\* \* \* \* \*